United States Patent
Zimmerman et al.

(10) Patent No.: US 8,280,735 B2
(45) Date of Patent: *Oct. 2, 2012

(54) TRANSCRIPTION DATA EXTRACTION

(75) Inventors: Roger S. Zimmerman, Wellesley, MA (US); Paul Egerman, Weston, MA (US); George Zavaliagkos, Acton, MA (US)

(73) Assignee: eScription Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,046

(22) Filed: Feb. 8, 2011

(65) Prior Publication Data

US 2012/0010883 A1  Jan. 12, 2012

Related U.S. Application Data

(63) Continuation of application No. 12/587,297, filed on Oct. 5, 2009, now Pat. No. 7,885,811, which is a continuation of application No. 11/080,689, filed on Mar. 14, 2005, now Pat. No. 7,613,610.

(51) Int. Cl.
*G10L 15/26* (2006.01)

(52) U.S. Cl. ............... 704/235; 704/9; 704/257; 704/10; 379/88.01; 379/88.02

(58) Field of Classification Search .................. 704/235, 704/9, 10, 2, 257, 260; 705/2, 3; 707/6, 707/5, 3; 279/88.01, 88.02; 379/88.01, 88.02
See application file for complete search history.

(56) References Cited

U.S. PATENT DOCUMENTS

| | | |
|---|---|---|
| 5,146,439 A | 9/1992 | Jachmann et al. |
| 5,519,808 A | 5/1996 | Benton, Jr. et al. |
| 5,602,982 A | 2/1997 | Judd et al. |
| 5,748,888 A | 5/1998 | Angelo et al. |
| 5,812,882 A | 9/1998 | Raji et al. |
| 5,857,212 A | 1/1999 | Van De Vanter |
| 5,875,448 A | 2/1999 | Boys et al. |
| 6,092,039 A * | 7/2000 | Zingher ................... 704/221 |
| 6,122,614 A * | 9/2000 | Kahn et al. ............... 704/235 |
| 6,374,225 B1 | 4/2002 | Hejna |
| 6,415,256 B1 | 7/2002 | Ditzik |
| 6,438,545 B1 | 8/2002 | Beauregard et al. |
| 6,687,339 B2 * | 2/2004 | Martin .................... 379/88.14 |
| 6,865,258 B1 | 3/2005 | Polcyn |
| 6,915,254 B1 * | 7/2005 | Heinze et al. ................. 704/9 |
| 6,950,994 B2 | 9/2005 | Dharap |
| 6,961,699 B1 | 11/2005 | Kahn et al. |

(Continued)

OTHER PUBLICATIONS

Batty et al., "The development of a portable real-time display of voice source characteristics," IEEE, 2:419-422 (2000).

*Primary Examiner* — Vijay B Chawan
(74) *Attorney, Agent, or Firm* — Wolf, Greenfield & Sacks, P.C.

(57) ABSTRACT

A computer program product, for performing data determination from medical record transcriptions, resides on a computer-readable medium and includes computer-readable instructions for causing a computer to obtain a medical transcription of a dictation, the dictation being from medical personnel and concerning a patient, analyze the transcription for an indicating phrase associated with a type of data desired to be determined from the transcription, the type of desired data being relevant to medical records, determine whether data indicated by text disposed proximately to the indicating phrase is of the desired type, and store an indication of the data if the data is of the desired type.

29 Claims, 6 Drawing Sheets

U.S. PATENT DOCUMENTS

| | | |
|---|---|---|
| 6,996,445 B1 | 2/2006 | Kamijo |
| 7,003,516 B2 | 2/2006 | Dehlinger et al. |
| 7,016,844 B2 | 3/2006 | Othmer et al. |
| 7,236,932 B1 | 6/2007 | Grajski |
| 2001/0033639 A1 * | 10/2001 | Martin .................. 379/88.14 |
| 2002/0178360 A1 * | 11/2002 | Wenocur et al. ............ 713/170 |
| 2002/0194501 A1 * | 12/2002 | Wenocur et al. ............ 713/201 |
| 2003/0046080 A1 | 3/2003 | Hejna, Jr. |
| 2003/0067495 A1 | 4/2003 | Pu et al. |
| 2005/0149747 A1 | 7/2005 | Wesinger, Jr. et al. |
| 2006/0206943 A1 | 9/2006 | Ellison et al. |
| 2006/0253895 A1 | 11/2006 | Brandofino et al. |
| 2006/0272025 A1 | 11/2006 | Mononen |
| 2007/0143857 A1 | 6/2007 | Ansari |
| 2007/0283444 A1 | 12/2007 | Jang |
| 2007/0294745 A1 | 12/2007 | Tan et al. |
| 2007/0300287 A1 | 12/2007 | Wynne et al. |

\* cited by examiner

TRANSCRIPTION DATA EXTRACTION

RELATED APPLICATIONS

This Application claims the benefit under 35 U.S.C. §120 and is a continuation (CON) of U.S. application Ser. No. 12/587,297 entitled "TRANSCRIPTION DATA EXTRACTION" filed on Oct. 5, 2009, which claims the benefit under 35 U.S.C. §120 and is a continuation (CON) of U.S. application Ser. No. 11/080,689, entitled "TRANSCRIPTION DATA EXTRACTION" filed on Mar. 14, 2005, each of which is herein incorporated by reference in its entirety.

BACKGROUND OF THE INVENTION

Healthcare costs in the United States account for a significant share of the GNP. The affordability of healthcare is of great concern to many Americans. Technological innovations offer an important leverage to reduce healthcare costs.

Many Healthcare institutions require doctors to keep accurate and detailed records concerning diagnosis and treatment of patients. Motivation for keeping such records include government regulations (such as Medicare and Medicaid regulations), desire for the best outcome for the patient, and mitigation of liability. The records include patient notes that reflect information that a doctor or other person adds to a patient record after a given diagnosis, patient interaction, lab test or the like.

Record keeping can be a time-consuming task, and the physician's time is valuable. The time required for a physician to hand-write or type patient notes can represent a significant expense. Verbal dictation of patient notes offers significant timesavings to physicians, and is becoming increasingly prevalent in modern healthcare organizations.

Over time, a significant industry has evolved around the transcription of medical dictation. Several companies produce special-purpose voice mailbox systems for storing medical dictation. These centralized systems hold voice mailboxes for a large number of physicians, each of whom can access a voice mailbox by dialing a phone number and putting in his or her identification code. These dictation voice mailbox systems are typically purchased or shared by healthcare institutions. Prices can be over $100,000 per voice mailbox system. Even at these prices, these centralized systems save healthcare institutions vast sums of money over the cost of maintaining records in a more distributed fashion.

Using today's voice mailbox medical dictation systems, when a doctor completes an interaction with a patient, the doctor calls a dictation voice mailbox, and dictates the records of the interaction with the patient. The voice mailbox is later accessed by a medical transcriptionist who listens to the audio and transcribes the audio into a text record. The playback of the audio data from the voice mailbox may be controlled by the transcriptionist through a set of foot pedals that mimic the action of the "forward", "play", and "rewind" buttons on a tape player. Should a transcriptionist hear an unfamiliar word, the standard practice is to stop the audio playback and look up the word in a printed dictionary.

Some medical transcriptionists may specialize in one area of medicine, or may deal primarily with a specific group of doctors. The level of familiarity with the doctors' voices and with the subject matter can increase the transcriptionist accuracy and efficiency over time.

The medical transcriptionist's time is less costly for the hospital than the doctor's time, and the medical transcriptionist is typically much more familiar with the computerized record-keeping systems than the doctor is, so this system offers a significant overall cost saving to the hospital.

To reduce costs further, health care organizations have deployed speech recognition technology, such as the AutoScript™ product (made by eScription™ of Needham, Mass.), to automatically transcribe medical dictations. Automatically transcribed medical records documents usually require editing by the transcriptionist. While speech recognition may accurately capture the literal word string spoken by the provider, the resulting document is generally not presented in a desired format.

Many new medical record documents could be or should be structured in tabular format with data values filled in to appropriate fields in the table. For example, laboratory reports, pathology reports, radiology reports and cardiac stress tests often can or should be wholly or partially formatted in tables with data filled in to the appropriate fields of the table.

In an exemplary scenario, a physician may dictate:

"patient's date of birth is January fifth, um let's see, ah, fifty three. Joe is a fifty one year old male who comes in today for a physical exam. On examination, his weight is one hundred eighty two pounds, BP is one twenty over eighty five. His general appearance is good."

It may be desired for the resulting portion of the document to appear as:

---

\*\*\*\*\*\*\*\*\*\*\*\*\*\*\*\*\*\*\*\*\*\*\*\*
Sex: Male
DOB: 01/05/1953
REASON FOR VISIT: Routine Physical.
PHYSICAL EXAMINATION:
General: Well-appearing
Pulse:
BP: 120/85
Weight: 182
Height:
\*\*\*\*\*\*\*\*\*\*\*\*\*\*\*\*\*\*\*\*\*\*\*\*\*\*\*\*\*\*\*\*\*\*\*\*\*\*\*\*\*\*

---

At least one automatic speech recognition system currently exists for formatting dictated data into tabular form. This existing system is an interactive speech recognition system where the medical care provider sees the data table on the screen and, therefore, knows what data is expected to be dictated and in what order. The speaker using this system must verbally indicate that the speaker is moving to the next tabular field (for example, by saying "next blank") before speaking the required data of the next field. Without interaction with the speaker, there is nothing to constrain the speaker to a particular sequence of dictating the desired information. Nor is there any way to guarantee that all required fields are available in the dictation when using the non-interactive system.

SUMMARY OF THE INVENTION

In general, in an aspect, the invention provides a computer program product for performing data determination from medical record transcriptions, the computer program product residing on a computer-readable medium and including computer-readable instructions for causing a computer to obtain a medical transcription of a dictation, the dictation being from medical personnel and concerning a patient, analyze the transcription for an indicating phrase associated with a type of data desired to be determined from the transcription, the type of desired data being relevant to medical records, determine whether data indicated by text disposed proximately to the indicating phrase is of the desired type, and store an indication of the data if the data is of the desired type.

Implementations of the invention may include one or more of the following features. The computer program product further includes instructions for causing the computer to alter a format of the transcription based upon whether the data indicated by the text disposed proximately to the indicating phrase is of the desired type. The computer program product further includes instructions for causing the computer to obtain a set of indicia of desired data types to be determined, and store data type indicators, and corresponding indicia of data from the transcription determined to be of desired types, in the transcription indicative of a table format such that if the transcription is displayed, the data indicia are displayed in association with corresponding data type indicators. The instructions allow for the determination of data corresponding to less than all of the desired data types indicated by the set of indicia, whereby the computer program product provides for sparse data extraction. The instructions for causing the computer to obtain the set of indicia cause the computer to retrieve the set in accordance with a worktype associated with the transcription.

Implementations of the invention may also include one or more of the following features. The data indicated by the text disposed proximately to the indicating phrase is determined to be of the desired type only if a probability of the proximately-disposed data being of the desired type exceeds a threshold probability. The data indicated by the text disposed proximately to the indicating phrase is determined to be of a first data type if a first probability that the proximately-disposed data is of the first data type exceeds a second probability that the proximately-disposed data is of a second data type. The computer program product further includes instructions for causing the computer to analyze information associated with patient to determine which type of data the indicated data are based on known relationships between values of different data types and patient information. The computer program product further includes instructions for causing the computer to obtain the information associated with the patient from the transcription.

Implementations of the invention may also include one or more of the following features. The computer program product further includes instructions for causing the computer to analyze the indicated data to determine which type of data the indicated data are based on known values of data associated with different data types. The computer program product further includes instructions for causing the computer to remove from the transcription, if it is determined that data indicated by text disposed proximately to the indicating phrase is of a desired type, the proximately-disposed text and the indicating phrase. The computer program product further includes instructions for causing the computer to modify the indicating phrase associated with the data type desired to be determined from the transcription. The instructions for causing the computer to determine if data indicated by text disposed proximately to the indicating phrase is of the desired type is capable of determining substantive data content of the text despite different phrases potentially forming the text.

In general, in another aspect, the invention provides a language processor module for processing a medical dictation transcription, the module being configured to compare words of the transcription with a plurality of natural language trigger phrases associated with desired types of data, make a probabilistic determination that the transcription includes first data of a first type if a first trigger phrase associated with the first type of data is found in the transcription, and alter the transcription, to produce an altered transcription, by at least one of removing the first trigger phrase from the transcription, and reformatting the transcription such that if the transcription is displayed the first data will be displayed in association with an indication of the first data type.

Implementations of the invention may include one or more of the following features. To make the probabilistic determination, the module is configured to compare the first data to at least one value associated with the particular data type. The module is configured to select the at least one value dependent upon patient information associated with a patient corresponding to the transcription. To alter the transcription the module is configured to produce a table including indicia of data types and the first data associated with the indication of the first data type. The module is configured to store the first data in a database field independent of the transcription. The trigger phrase comprises a natural language phrase. At least a portion of the transcription is normalized and the trigger phrase comprises a normalized language phrase. The module is configured to remove the first trigger phrase and indicia of the first data from the transcription. To make a probabilistic determination the module is configured to analyze a first probability that the first data represents the desired data type and a second probability that the first data represents another data type. To make a probabilistic determination the module is configured to determine that a probability that the first data represents the first data type exceeds a probability threshold.

Various aspects of the invention may provide one or more of the following capabilities. Time and cost of editing automatically-generated medical transcription documents can be reduced. Transcriptionist fatigue in editing transcribed documents can be reduced. Data can be extracted from a document dictated in a natural manner and entered as a by-product of current dictation work flow into tabular form and/or into individually specific data fields. Costs associated with entering data into an electronic medical record can be reduced. Medical records can be used to better track patient progress and/or can be more easily searched to assist in medical treatment outcome research. Data from medical record transcriptions can be extracted and used without substantially interfering with normal work flow of the providers of medical care providing the medical records dictations. Medical record documents can be provided with an improved appearance. The creation of fully electronic medical records can be facilitated.

These and other capabilities of the invention, along with the invention itself, will be more fully understood after a review of the following figures, detailed description, and claims.

DETAILED DESCRIPTION OF PREFERRED EMBODIMENTS

Embodiments of the invention provide techniques for extracting specific data elements as a result of automated speech recognition of medical dictations. For example, an automatic speech recognition (ASR) system is supplemented by natural language processing, constrained by one or more tables of data elements for locating relevant information in the dictation. The natural language processing analyzes the dictation and extracts data according to the desired table, preferably without interaction with the speaker and preferably without the speaker dictating the data for the table in any particular sequence. The extracted data may be presented along with original audio, to a medical transcriptionist (MT) for editing. Other embodiments are within the scope of the invention.

Figure 1:
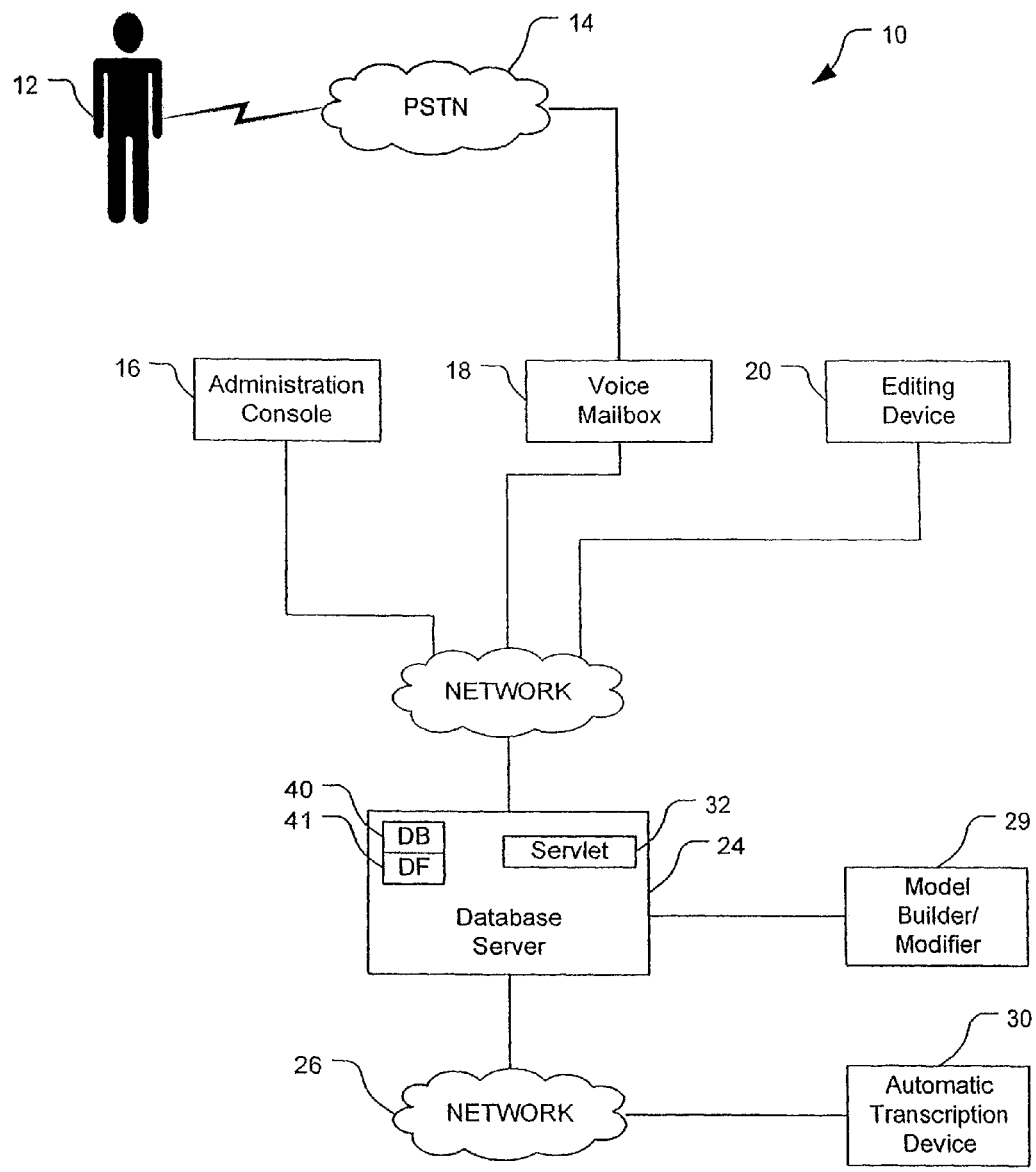
FIG. 1 is a simplified diagram of a system for transcribing dictations and editing corresponding transcriptions.

Referring to FIG. 1, a system 10 for transcribing audio and editing transcribed audio includes a speaker/person 12, a communications network 14, a voice mailbox system 16, an administrative console 18, an editing device 20, a communications network 22, a database server 24, a communications network 26, a model builder/modifier 29, and an automatic transcription device 30. Here, the network 14 is preferably a public switched telephone network (PSTN) although other networks, including packet-switched networks could be used, e.g., if the speaker 12 uses an Internet phone for dictation. The network 22 is preferably a packet-switched network such as the global packet-switched network known as the Internet. The network 26 is preferably a packet-switched, local area network (LAN). Other types of networks may be used, however, for the networks 14, 22, 26, or any or all of the networks 14, 22, 26 may be eliminated, e.g., if items shown in FIG. 1 are combined or eliminated. As discussed below, the model builder/modifier 29 is configured to build and/or modify models (e.g., trigger models, content models, order models) used to accurately extract the requested data fields from the transcription.

Preferably, the voice mailbox system 16, the administrative console 18, and the editing device 20 are situated "off site" from the database server 24 and the automatic transcription device 30. These systems/devices 16, 18, 20, however, could be located "on site," and communications between them may take place, e.g., over a local area network. Similarly, it is possible to locate the automatic transcription device 30 off-site, and have the device 30 communicate with the database server 24 over the network 22.

The network 14 is configured to convey dictation from the speaker 12 to the voice mailbox system 16. Preferably, the speaker 12 dictates into an audio transducer such as a telephone, and the transduced audio is transmitted over the telephone network 14 into the voice mailbox system 16, such as the Intelliscript™ product made by eScription™ of Needham, Mass. The speaker 12 may, however, use means other than a standard telephone for creating the digital audio file for each dictation. For example, the speaker 12 may dictate into a handheld PDA device that includes its own digitization mechanism for storing the audio file. Or, the speaker 12 may use a standard "dictation station," such as those provided by many vendors. Still other devices may be used by the speaker 12 for dictating, and possibly digitizing the dictation, and sending it to the voice mailbox system 16.

The voice mailbox system 16 is configured to digitize audio from the speaker 12 to produce a digital audio file of the dictation. For example, the system 16 may use the Intelliscript™ product made by eScription.

The voice mailbox system 16 is further configured to prompt the speaker 12 to enter an identification code and a worktype code. The speaker 12 can enter the codes, e.g., by pressing buttons on a telephone to send DTMF tones, or by speaking the codes into the telephone. The system 16 may provide speech recognition to convert the spoken codes into a digital identification code and a digital worktype code. The mailbox system 16 is further configured to store the identifying code and the worktype code in association with the dictation. The identification code can associate the dictation with a particular speaker and/or an entity associated with the speaker (e.g., the speaker's employer or affiliate hospital, etc.). Speakers with multiple affiliations (e.g., to different entities such as hospitals) preferably have multiple identification codes, with each identification code corresponding to a respective one of the affiliated entities. The system 16 preferably prompts the speaker 12 to provide the worktype code at least for each dictation related to the medical field. The worktype code designates a category of work to which the dictation pertains, e.g., for medical applications this could include Office Note, Consultation, Operative Note, Discharge Summary, Radiology report, etc. The worktype code may be used to define settings such as database fields and/or to refine settings, such that settings may be specific not only to speaker-transcriptionist pairings, but further to worktype of dictations provided by the speaker, and/or to other parameters or indicia.

The voice mailbox system 16 is further configured to transmit the digital audio file and speaker identification code and worktype code over the network 22 to the database server 24 for storage. This transmission is accomplished by the system 16 product using standard network transmission protocols communicating with the database server 24.

The database server 24 is configured to store the incoming data from the voice mailbox system 16, as well as from other sources, in a database 40. The database server 24 may include the EditScript™ database product from eScription. Software of the database server is configured to produce a database record for the dictation, including a file pointer to the digital audio data, and a field containing the identification code for the speaker 12. If the audio and identifying data are stored on a PDA, the PDA may be connected to a computer running the HandiScript™ software product made by eScription that will perform the data transfer and communication with the database server 24 to enable a database record to be produced for the dictation.

The database 40 stores a variety of information regarding transcriptions. The database 40 stores the incoming data from the voice mailbox system 16, the database record produced by the database software, data fields associated with transcriptions, etc. The data fields are stored in a tabular data fields section 41, of the database 40, that includes sets of data fields associated with particular transcriptions. These fields may be accessed by the automatic transcription device 30, e.g., for storing data in the fields, or the administration console 18, e.g., for searching the fields for particular information.

Preferably, all communication with the database server 24 is intermediated by a "servlet" application 32 that includes an in-memory cached representation of recent database entries. The servlet 32 is configured to service requests from the voice mailbox system 16, the automatic transcription device, the editing device 20, and the administrative console 18, reading from the database 40 when the servlet's cache does not contain the required information. The servlet 32 includes a separate software module that helps ensure that the servlet's cache is synchronized with the contents of the database 40. This helps allow the database 40 to be off-loaded of much of the real-time data-communication and to grow to be much larger than otherwise possible. For simplicity, however, the below discussion does not refer to the servlet, but all database access activities may be realized using the servlet application 32 as an intermediary.

The automatic transcription device 30 may access the database in the database server 24 over the data network 26 for transcribing the stored dictation. The automatic transcription device 30 uses an automatic speech recognition (ASR) device (e.g., software) to produce a draft transcription for the dictation. An example of ASR technology is the AutoScript™ product made by eScription, that also uses the speaker identifying information to access speaker-dependent ASR models with which to perform the transcription. The device 30 transmits the draft transcription over the data network 26 to the database server 24 for storage in the database and to be accessed, along with the digital audio file, by the editing device 20.

The editing device 20 is configured to be used by a transcriptionist to access and edit the draft transcription stored in the database of the database server 24. The editing device 20 includes a computer (e.g., display, keyboard, mouse, monitor, memory, and a processor, etc.), an attached foot-pedal, and appropriate software such as the EditScript Client™ software product made by eScription. The transcriptionist can request a dictation job by, e.g., clicking an on-screen icon. The request is serviced by the database server 24, which finds the dictation for the transcriptionist, and transmits the corresponding audio file and the draft transcription text file, as stored in the database.

The transcriptionist edits the draft using the editing device 20 and sends the edited transcript back to the database server 24. For example, to end the editing session the transcriptionist can click an on-screen icon button to instruct the editing device 20 to send the final edited document to the database server 24 via the network 22, along with a unique identifier for the transcriptionist.

With the data sent from the editing device 20, the database in the server 24 contains, for each dictation: a speaker identifier, a transcriptionist identifier, the digital audio signal, and the edited text document.

The edited text document can be transmitted directly to a customer's medical record system or accessed over the data network 22 from the database by the administrative console 18. The console 18 may include an administrative console software product such as Emon™ made by eScription.

The raw and edited versions of a transcription may be used by the model builder/modifier 29 to models for data extraction. The raw and edited versions of transcriptions associated with their respective speakers are stored in the database 40. The model builder/modifier 29 uses the transcriptions for each speaker to build or modify models for the speaker (and/or speaker and worktype) for extracting data from transcriptions. These models are stored in the database 40 so that they may be accessed and used by the automatic transcription device 30 to extract data from transcriptions.

Figure 2:
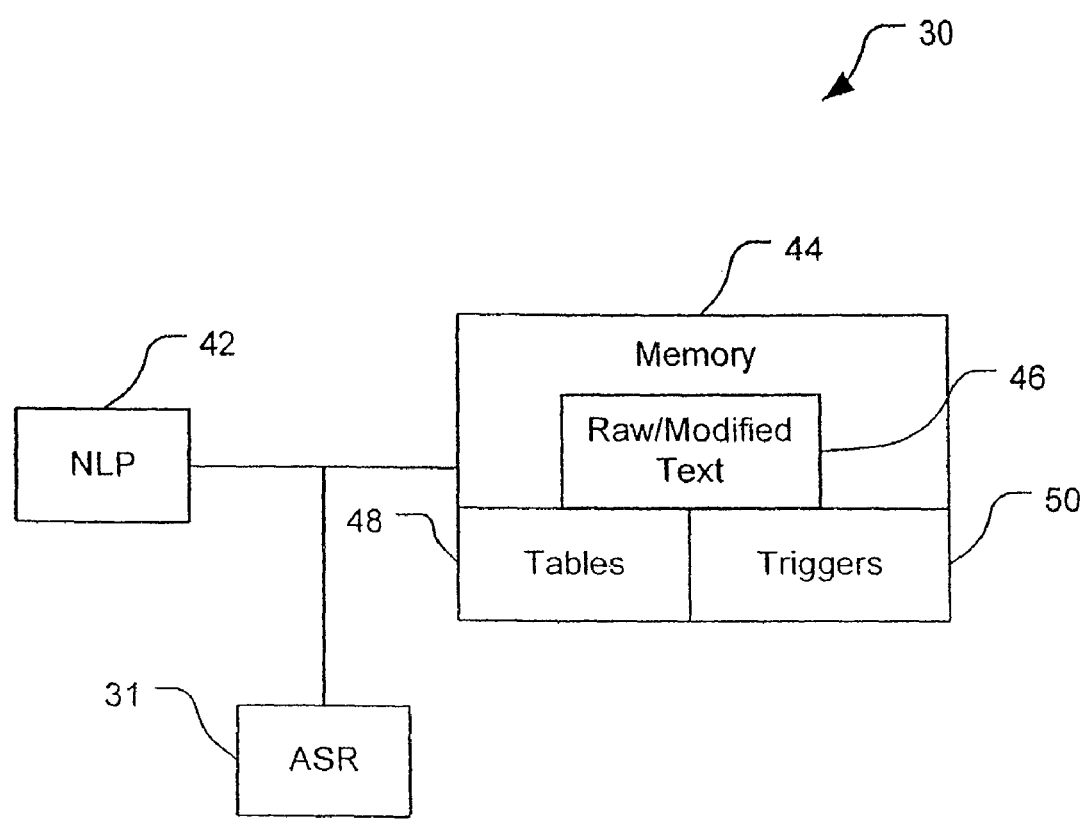
FIG. 2 is a block diagram of components of an automatic transcription device shown in FIG. 1.

Referring also to FIG. 2, the automatic transcription device 30 includes an ASR module 31, a memory 44, and a natural language processing module (NLP) 42. The NLP module 42 includes memory and a processor for reading software code stored in the memory and for executing instructions associated with this code for performing functions described below. The NLP module 42 is configured to analyze raw transcribed speech data from the automatic transcription device 30 to extract data elements from the transcribed text, and possibly use the extracted data to fill in a table or database fields. The memory 44 includes a raw/modified text section 46, a table section 48, and a trigger section 50. The raw/modified text section 46 includes the stored raw text of the speech-recognized transcription and the corresponding text as modified by the NLP module 42. The table section 48 includes stored tables that may be desired to be filled in with data extracted from various transcriptions. The trigger section 50 includes triggers corresponding to particular types of data desired to be extracted from the transcriptions in accordance with the tables stored in the table section 48. Trigger models may be built and/or modified by the model builder/modifier 29 (FIG. 1).

Figure 3:
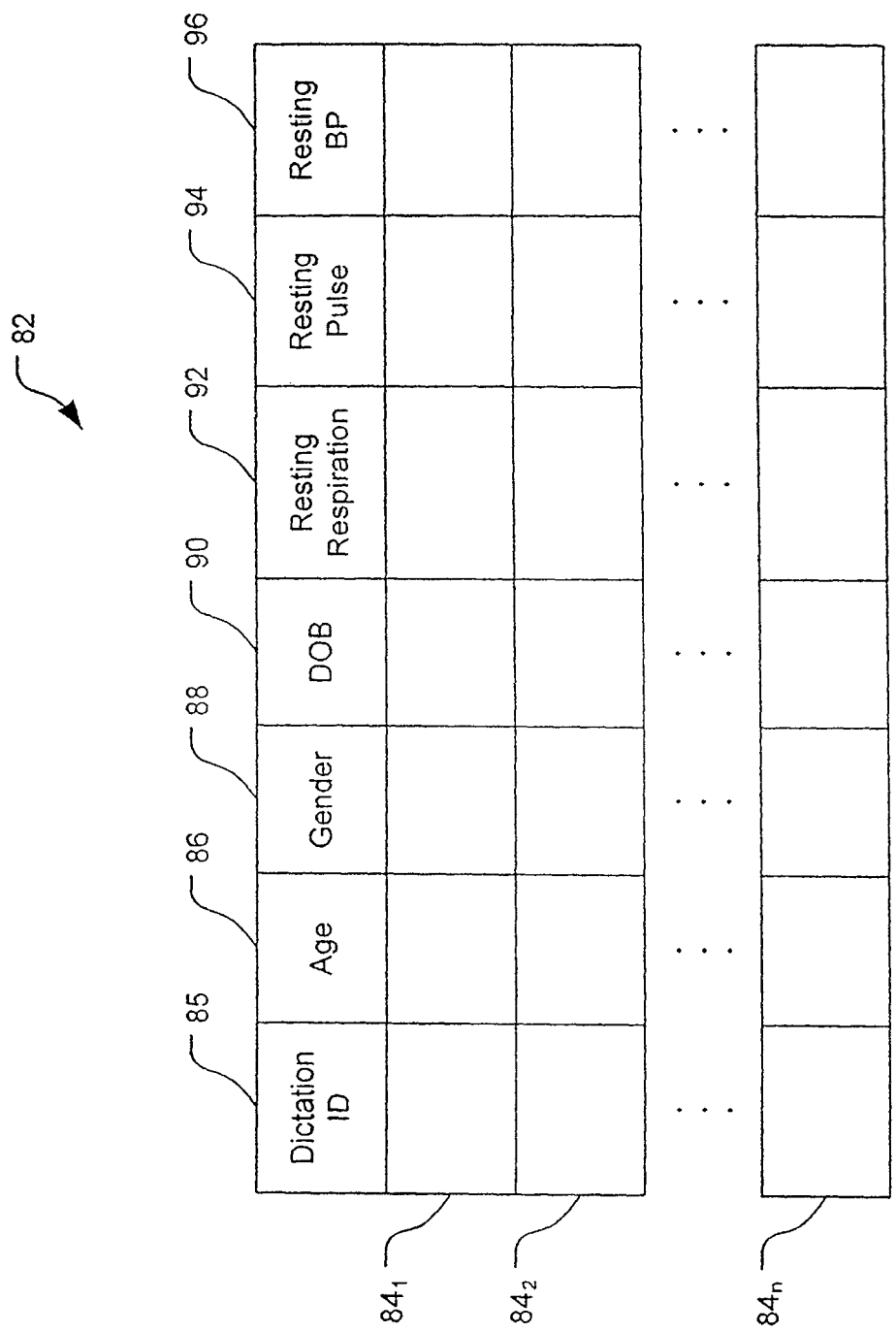
FIG. 3 is a simplified portion of an exemplary database table of data fields associated with medical transcriptions.

Referring to FIG. 3, an exemplary database 82 of tabular data stored in the tabular data fields section 41 of the database 40 (FIG. 1) associated with corresponding transcriptions includes data sets 84 with dictation identifications 85 and several data fields, here data fields 86, 88, 90, 92, 94, 96. The dictation identification is uniquely associated with a corresponding dictation and the data fields are preferably in sets corresponding to the type of transcription, e.g., here being for medical record transcriptions. Thus, in this example, the database 82 includes data sets 84 each with data in an age data field 86, a gender data field 88, a date of birth (DOB) data field 90, a resting respiration data field 92, a resting pulse data field 94, and a resting blood pressure data field 96. The data fields 86, 88, 90, 92, 94, 96 are searchable, e.g., using known database search techniques on the database 82. The data sets 84 each correspond to a separate transcription and the corresponding data fields are populated with the data extracted from the associated transcription. Information stored in the data fields 86, 88, 90, 92, 94, 96 may be extracted from transcriptions and/or entered independently (e.g., through the administration console 18 shown in FIG. 1).

Referring again to FIGS. 1-2, the NLP module 42 is configured to access a table to be filled in with data extracted from a transcription. For example, the NLP module 42 can access a particular table from the table section 48 in accordance with the worktype code entered by the speaker. Other techniques, however, may be used to determine which table to access to be filled in with data extracted from the transcription. For example, one or more tables may be associated with a particular speaker through the identification code, or tables may be accessed in accordance with a combination of identification code and worktype code, or worktype code alone, etc.

Fields of the table(s) accessed by the NLP module 42 are associated with corresponding "trigger" phrases stored in the trigger section 50. A trigger phrase provides context for data and may include a single word or character (e.g., a symbol such as a number sign (#), the symbol for feet ('), or the symbol for inches (")), multiple or characters, or combinations of one or more words and one or more characters. A trigger phrase indicates that the transcription likely contains desired data in the vicinity of the trigger phrase. The trigger phrases may be stored in sets that are associated with corresponding ones of the tables in the table section 48, or may be stored individually and associated with any table that includes a field corresponding with the particular trigger phrase, etc. The trigger phrases may be predictive, (e.g., "the blood pressure is _"), retroactive (e.g., _____ beats per minute"), or both (e.g., "temperature is _____ degrees orally"). Several passes can be made over the transcribed text by the NLP module 42 to refine the search for table data, especially if the NLP module 42 is operating as a background ASR, and is therefore not operating as a real-time interactive processing module. The NLP module 42 may assess the tabular data fields to be filled in or data otherwise to be extracted from the transcription based on various probabilities that the data corresponds to desired table or other data to be extracted, potentially both of the data field in question as well as other data fields.

The NLP module 42 may use the trigger phrases in a variety of manners in order to extract data from the transcription, preferably to help improve the accuracy with which data are extracted from the transcription. For example, the triggers may be probabilistically weighted based on various parameters such as speaker-specific or speaker-independent textual data. For example, a different trigger phrase may be associated with a number of different table items potentially, with different likelihoods associated with the different potential table items. The different probabilities associated with the different data items may be speaker independent or speaker dependent. For example, given the existence of a trigger phrase in the transcription of "the patient is," the subsequent data may be the age with 80% probability, or height with 15% probability, or appearance with 5% probability. These probabilities are exemplary, and may be different in practice, especially for different speakers. Further, the NLP module 42 may train trigger phrases using natural ASR raw data output so that the trigger phrases can incorporate or accommodate typical errors. Usually, such a trigger model would be a speaker-specific model. Additionally, the NLP module 42 may use a single trigger phrase to extract data for multiple data fields. For example, a medical care provider may dictate "vital signs one hundred over sixty, eighty-two and regular." The NLP Module 42 may analyze the use of the trigger phrase "vital signs" as an indicator of both blood pressure and pulse.

The NLP module 42 is further configured to analyze the transcription in view of a content model to help modify transcribed text into common formats, taking account of different manners in which different speakers may say the same thing. The NLP 42 can thus make the format of various types of data be presented consistently despite inconsistent manners in which the data is spoken. For example, one speaker may say "The patient's temperature was one hundred and one point three degrees" while another speaker may say "The patient's temperature was one oh one three." The data, the patient's temperature of 101.3° F. is the same, but the text is different in these two examples. The NLP module 42 applying a content model built and/or modified by the model builder/modifier 29 can analyze these two different texts and modify the transcription to produce a consistent edited text, e.g., of 101.3° F. Examples of different styles of speech for conveying similar information that the NLP module 42 can preferably make consistent are:

1) Body Temperature

The content model can accept the speaker saying ninety, or some form of a hundred, followed by either a digit, or the word point followed by a digit. The content model would further be able to identify digits (e.g., "zero" and "oh") and distinguish between digits and non-digits (e.g., "two" versus "too").

2) Date

The content model can accept various manners for specifying month, day, and year. The content model can recognize numeric or name specifications of months (e.g., "three" versus "March") and various manners of specifying days (e.g., "five" versus "fifth") and years (e.g., "oh five" versus "two thousand five" versus "two thousand and five") as well as month-year combinations (e.g., "March two thousand five" versus "March of two thousand five").

Preferably, the NLP module 42 can apply the content model to these various texts to deduce the underlying data and present the underlying data in a consistent manner for each of the exemplary pairs of alternate expressions shown, as well as other alternative texts for conveying the same data, or other data or data types (i.e., the examples shown are exemplary only, not exclusive, and not required).

Content models provided by the model builder/modifier 29 can be based on allowable grammars. Per-speaker probabilities can be assigned to "paths" through a grammar based on how the speaker dictates each data type. The model builder/modifier 29 can compute these probabilities and build/modify the content models using these probabilities, preferably offline.

The NLP module 42 may also apply syntax constraints to the ASR output associated with particular types of data. Applying these constraints can help resolve ambiguity when the same trigger phrase is potentially used to indicate different types of data. For example, if a trigger phrase could be used to indicate either a pulse or a respiratory rate, then the NLP module 42 prefers pulse if the transcription contained a numeric quantity greater than 30 and a respiratory rate otherwise. Thus, the NLP module 42 applies constraints based on known characteristics and/or likely values (e.g., ranges) of the various parameters or data types that the data may be in order to select which data type corresponds to particular data in a transcription. Further, the syntax constraints may lead to content models not employing non-absolute probabilities (i.e., probabilities greater than 0% and less than 100%) for some or all instances associated with the models. For example, to evaluate a transcription for a blood pressure value, if the transcription does not contain text in the form of a first number, followed by the word "over," followed by a second number that is smaller than the first, then the model would not assign a value to a blood pressure variable. This may, however, be viewed as a 0% probability and thus an implementation of probabilities. If the first number "over" second number syntax is found, then the value for blood pressure would be hypothesized, with the probability of this being true being computed from the trigger model and order model (discussed below).

Further, the NLP module 42 is configured to use information about the subject of the transcription (e.g., a patient) available from the transcription or otherwise to constrain the search for given data types. For example, the transcription may indicate, or it may be otherwise known that (e.g., independently entered or determined that), the patient is a 47-year old male. In this case, certain values for the patient's weight and height would be deemed more likely to be correct if they comport with values for these data types typically associated with a 47-year old male. For example, a value of higher than 60 inches may be deemed to be more likely to be indicative of the patient's height and a value of 120 or more may be deemed to be more likely to be associated with the patient's weight. Additionally, the data search process performed by the NLP module 42 could be supplemented by providing access by the NLP module 42 to the patient's historical data from medical records, e.g., stored in the database 40. This information could be obtained either by having the speaker enter a patient-identifying code (such as the patient's medical record number (MRN)) with each dictation or by extracting this information from the spoken dictation, etc. Once the patient identification is obtained, the NLP module 42 may query the patient's historical medical data, and use this data to limit or constrain searches for valid content words (i.e., the words indicative of data values). For example, the search for blood pressure, cholesterol values, birth date, height, weight, etc. could benefit from constrained searches based upon information about the patient.

The NLP module 42 may further employ a model when analyzing the transcription in accordance with the order in which the speaker dictates the table fields and expected orders for such dictations. For example, the NLP module 42 may employ an n-gram formulation to analyze the n previous data fields that were extracted and determine a probability for the next data field being any of various potential data fields. Thus, the NLP module 42 employing a 3-gram formulation can determine the likelihood that the speaker is about to dictate the blood pressure field conditioned on the preceding two fields dictated being the patient's pulse and respiratory rate. This model may be deterministic and thus require a specific sequence of data fields or may be non-deterministic/probabilistic, not requiring a particular sequence of data fields. Such a model assists the search by attributing a probability to each possible dictation sequence to increase the likelihood that particular data in the transcription is accurately extracted from the transcription, e.g., and stored in an appropriate data field and/or table entry.

The model builder/modifier 29 may produce custom trigger models for use in analyzing the transcription. For example, the database 40 may contain the history of text documents produced from the speaker's dictations, as well as the automatic transcriptions of the speaker's dictations provided by the automatic transcription device 30. The trigger phrases and content word syntax for each data type dictated by the speaker can be derived by correlating the final documents with the raw transcriptions, in effect reversing the decoding process to determine trigger phrases from the content words used by the speaker. The trigger models used by the NLP module 42 can be updated, e.g., periodically, as more dictations are gathered for the speaker over time. In this way, the models can track changes in the speaker's speaking style. The NLP module 42 preferably uses the updated model for the next transcription to be analyzed from the particular speaker. The NLP module 42, however, could re-evaluate a transcription from the speaker that was the last transcription analyzed before the trigger model was updated (e.g., the transcription that induced the update in the trigger model). Further, the model builder/modifier 29 may weight more recent transcriptions from the speaker more heavily than earlier transcriptions to help account for changes in the speaker's style.

Further, the NLP module 42 may not fill all of the data fields desired to be extracted (e.g., associated with a particular table at issue), as the speaker may not dictate data corresponding to all of the data fields and/or may not dictate the data with sufficient confidence that the NLP module 42 fills all the data fields. For example, the NLP module 42 may not fill a data field associated with a table if data from the transcription has an undesirably low probability of being associated with a particular data field. Thus, the NLP module 42 may leave the raw text of the transcription intact and not fill a data field if the highest probability of data in the transcription being associated with that data field does not meet or exceed a threshold probability value. In this case, the "free text" form of the transcription may be left alone such that the MT can choose to move data from the text into a particular data field (e.g., in a table) as appropriate. The NLP module 42 thus can provide a sparse data extraction process where the speaker may not dictate all desired data items or may not dictate all desired data items with sufficient confidence for the NLP module 42 to associate the dictated data with particular data fields.

Figure 4:
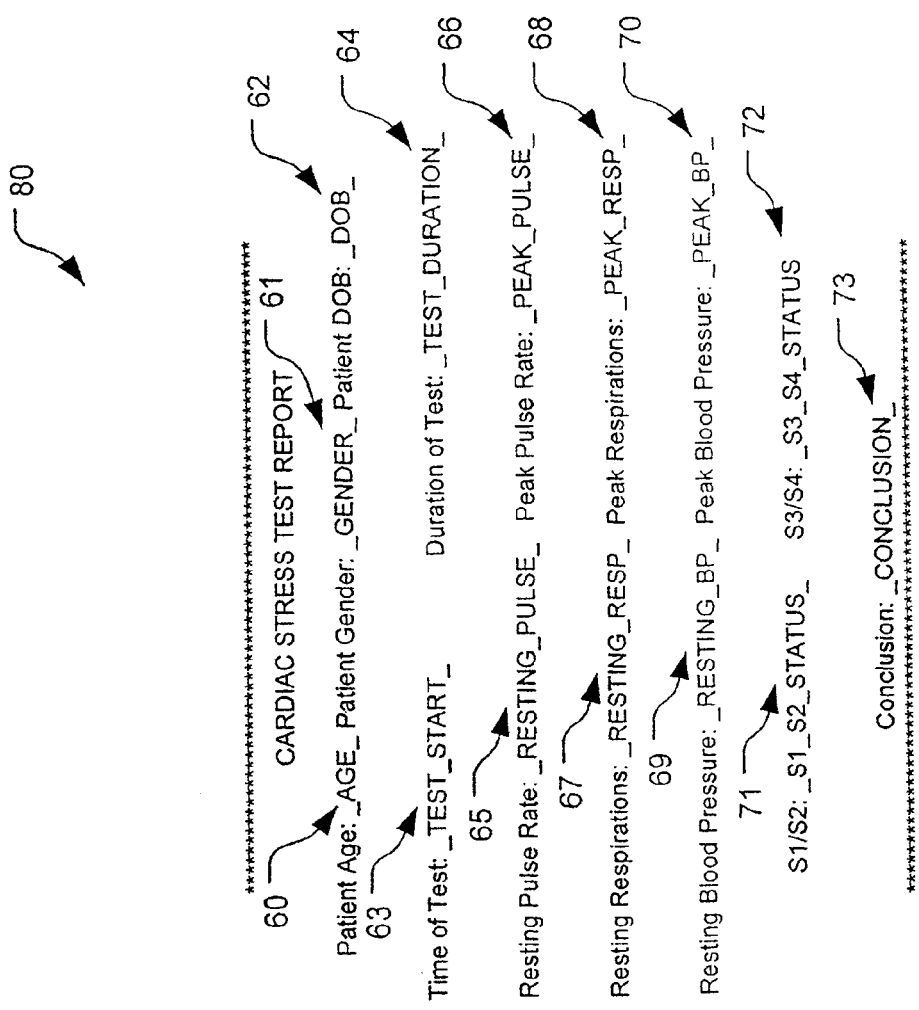
FIG. 4 is an exemplary portion of a table for use in a medical transcription.

Referring also to FIG. 4, the table structure may be encoded or stored as a combination of literal text and data-type tags, e.g., tags 60-73 as shown. The data-type tags 60-73 may be limited in any variety of manners, e.g., with underscores on either side of the tags 60-73 as shown in FIG. 4 to separate the tags 60-73 from the literal text. FIG. 4 illustrates a portion 80 of an exemplary encoded table and is not limiting of the invention.

The NLP module 42 attempts to replace all of the data-type tags 60-73 in the table portion 80 with appropriate data items extracted from the transcription. The NLP module 42 further attempts to exclude the raw text associated with these items from which the data for the corresponding data fields is drawn. The transcription is thus edited to remove the text indicative of the data, and the table portion 80 is updated with the data extracted from the raw text.

The table portion 80 illustrates the generality of potential table data fields. The table fields need not be restricted to numeric data. For example, descriptive data may be appropriate for some of the fields (e.g., the _s1_s2_STATUS field 71 may have a value of "normal"). Other fields may be filled with other text including full paragraphs (e.g., the _CONCLUSION_field 73 may have a value of "This is a problematic test. The patient should be considered for cardiac angiography in the next few days.").

Figure 5:
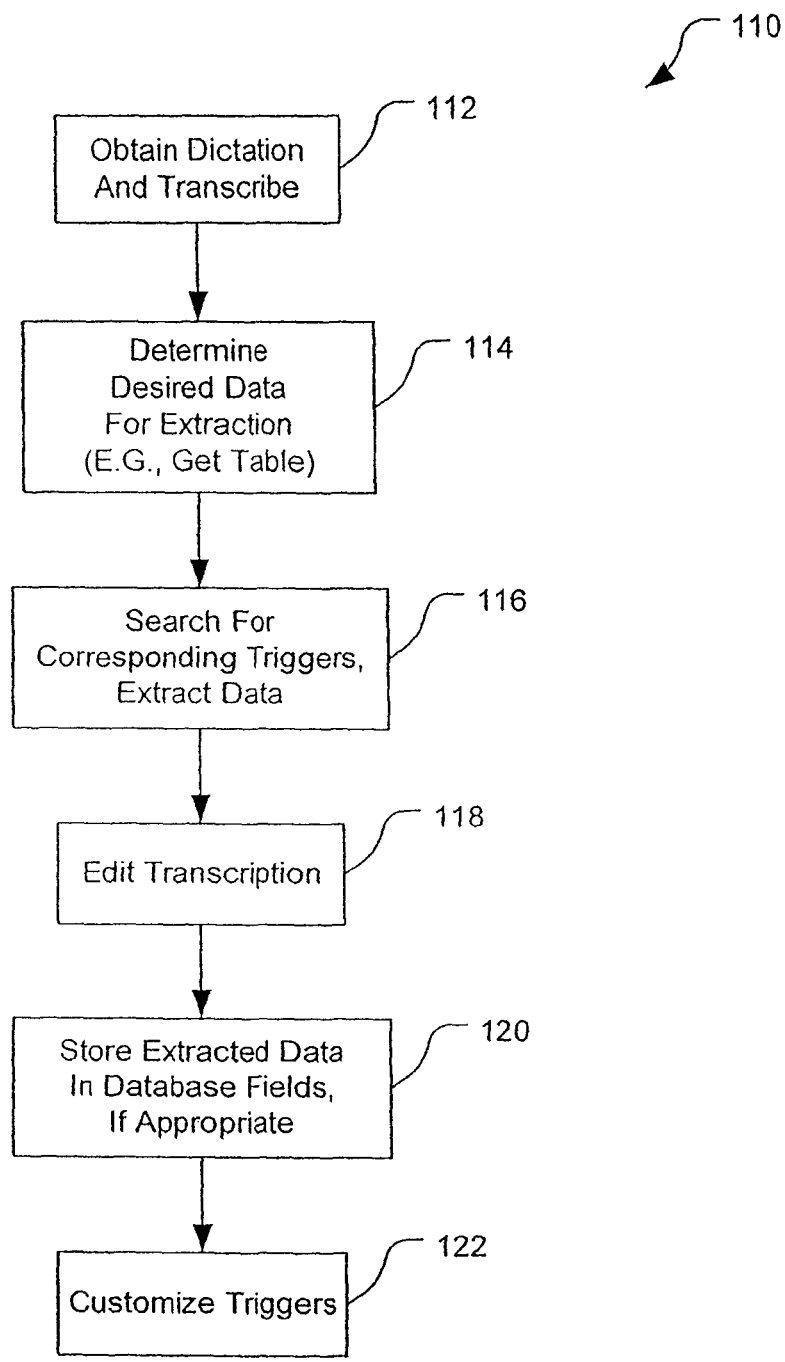
FIG. 5 is a block flow diagram of a process of performing sparse data extraction.

Referring to FIG. 5, with further reference to FIGS. 1-2, a process 110 of performing sparse data extraction using system 10, and in particular the NLP module 42, includes the stages shown. The process 110, however, is exemplary only and not limiting. The process 110 can be altered, e.g., by having stages added, removed, or rearranged.

At stage 112, dictation is obtained and transcribed. The speaker 12 dictates text that is conveyed through the network 14 to, and stored in, the voice mailbox 16. The dictation is conveyed through the network 22, the database server 24, and the LAN 26 to the automatic transcription device 30. The device 30 transcribes the stored dictation and provides the transcribed text to the memory 44 where it is stored in the raw/edited text section 46.

At stage 114, the NLP module 42 determines the desired data for extraction. For example, if the data to be extracted corresponds to a table, then the NLP module 42 accesses the appropriate table from the table section 48 of the database 40. The NLP module 42 accesses the appropriate table, e.g., by searching for a table corresponding to the worktype code and/or the identification code entered by the speaker 12 or transcribed from the dictation from the speaker 12. The table that is accessed provides indicia of the data fields to be extracted from the transcription for filling in the table, with the data fields being associated with corresponding trigger phrases.

At stage 116, the NLP module 42 searches for triggers in the raw transcription corresponding to the data desired to be extracted and extracts the data. For each data type desired by the table, the raw text transcription is searched by the NLP module 42 for potential triggers, and the adjacent content words are assigned likelihoods for being one or more of the desired data fields based on the posterior trigger probability and the syntax likelihood of the content words. Multiple possible parses of the raw text transcription are scored and preferably the best fit between the table structure and the trigger and content words is found. For each data type accounted for in the best-fit parse, the corresponding table fields are filled in and the corresponding trigger and content words are removed from the raw text transcription. The best-fit may be a table-wide best fit, a partial-table best fit, or may be the best fit for each individual data field.

The following example is provided to illustrate multiple potential parses being applied to a portion of transcribed text for determining data fields. A portion of an exemplary raw text transcription may read:

This is a cardiac stress test on John Doe that lasted 37 minutes. He is 46-year-old male. I don't have the date of birth available at this time. The test was performed at 11:00 A.M. where the patient's pulse was measured at 87 bpm. BP 150/85. After 20 minutes, rate was up to 145. S1/S2 normal. The other heart sounds were normal.

Two exemplary potential parses for this transcription fragment are as follows:

a) This is a cardiac stress test on John Doe which lasted 37 minutes. TRIGGER_PATIENT_AGE_ _PATIENT_AGE_. Male. I don't have the date of birth available at this time. TRIGGER_TEST_START_ _TEST_START_TRIGGER_RESTING_PULSE_ _RESTING_PULSE_ TRIGGER_RESTING_BP_RESTING_BP_. After twenty minutes, TRIGGER_PEAK_PULSE_PEAK_PULSE_. TRIGGER_S1_S2_STATUS_ _S1_S2_STATUS_. The other heart sounds were normal.

b) This is a cardiac stress test on John Doe TRIGGER_TEST_DURATION_TEST_DURATION_. He is a 46-year-old male. I don't have the date of birth available at this time. TRIGGER_TEST_START_ _TEST_START_TRIGGER_PEAK_PULSE_ _PEAK_PULSE_TRIGGER_RESTING_BP_ _RESTING_BP_. After twenty minutes, rate was up to 145. TRIGGER_S1_S2_STATUS_S1_S2_STATUS_. The other heart sounds were normal.

In these parses, where a trigger phrase or data type is hypothesized, the underlying raw text words appearing in the transcription raw text (either the trigger phrase or content words) are subsumed, so that they do not appear in the document as hypothesized. Also, each trigger phrase and data type in the parses has an associated probability, so that standard search techniques, such as Viterbi decode, may be applied to the entire sequence to try to find the parse with the higher/highest overall probability. If the first parse is chosen as the more likely parse by the search, then the corresponding section of the output might appear as follows:

---
CARDIAC STRESS TEST REPORT
Patient Age: 46 Patient Gender: _____ Patient DOB: _____
Time of Test: 11:00 a.m. Duration of Test: _____
Resting Pulse Rate: 87 Peak Pulse Rate: 145
Resting Respirations: _____ Peak Respirations: ---------
Resting Blood Pressure: 150/85 Peak Blood Pressure: _____
S1/S2: Normal.                    S3/S4: _____
--------------------------------------------
This is a cardiac stress test on John Doe which lasted 37 minutes.
Male.
I don't have the date of birth available at this time.
After twenty minutes,
The other heart sounds were normal.

---

The text below the dash line is fragmented because trigger phrases and content words have been removed. This text can be used by the transcriptionist to potentially ease the task of filling in any data fields not filled in automatically by the NLP module 42. Alternatively, the text below the dashed line could be deleted, with the MT filling in the remaining fields that have been dictated by the speaker using the audio played to the MT. Alternatively still, some of the text may be deleted while other portions of the text may be provided to the MT. For example, the phrase "after twenty minutes" may possibly be removed as this text portion is a sentence fragment.

The draft transcription at this point is a modified (from the raw text), partially-structured, transcription ready for uploading. The modified transcription includes a structured document, to the extent it has been filled in by the NLP module 42, and the remaining raw text, to the extent that it has been deemed worth including in the draft. Subsequent formatting steps can be applied to the remaining raw text, that may include text that does not contribute to the structured part of the document. The draft in this stage is preferably uploaded to the database 40.

At stage 118, the draft transcription is edited by the medical transcriptionist. The MT retrieves the draft transcription stored in the database 40 via the network 22. The MT edits the draft transcription using the editing device 20. This editing includes modifying data that was extracted from the transcribed text, e.g., including modifying data entries for a table. Further, the editing may include adding information that was not extracted from the text, including adding data to the table where data was not dictated corresponding to one or more data fields.

At stage 120, the extracted and/or edited and/or added data is stored in the appropriate database fields. The extracted or otherwise provided data from the editing device 20 is stored in corresponding database fields in the tabular data field section 41 of the database 40. For example, age, gender, date of birth, resting respiration, resting pulse and/or resting blood pressure is stored in the corresponding database fields 86, 88, 92, 94, 96 in an appropriate entry 84 of the database 82. The database fields and the data in these fields may be accessed separately, including independently of the NLP Module 42.

At stage 122, trigger phrases are customized by the model builder/modifier 29. The edited transcription can be compared by the NLP module 42 with the draft transcription provided by the NLP module 42 to determine whether data determined by the NLP module 42 corresponding with a particular data field was changed by the medical transcriptionist. Using this information, the NLP module 42 can modify the trigger phrases and/or models used to associate the extracted data with the corresponding data fields. Thus, trigger phrases and/or trigger models can be modified to accommodate changes in style of speakers and/or trigger phrases used by the speaker, or multiple speakers associated with a common entity, etc. The NLP module 42 would then apply the modified trigger phrases and/or trigger models and/or other models provided/modified by the model builder/modifier 29 (or otherwise provided, e.g., stored in the memory 44) to future analyses of transcriptions to perform sparse data extraction on the transcriptions.

The process 110 can be modified and, as such, the process illustrated in FIG. 5 as described above is illustrative only. For example, the extracted data may be stored before the transcription is edited by the medical transcriptionist and the data modified, if at all, by the medical transcriptionist and re-stored subsequent to the transcription editing.

Figure 6:
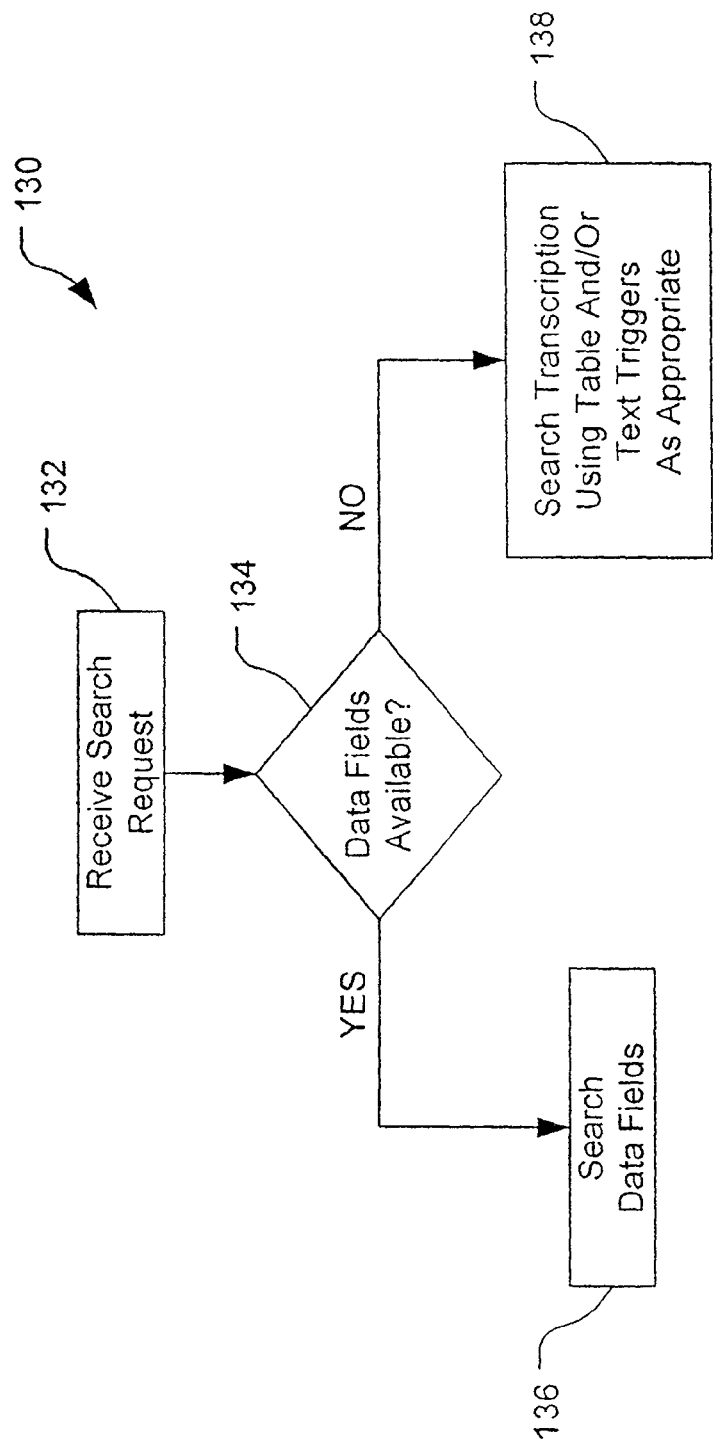
FIG. 6 is a block flow diagram of a process of searching for data extracted from, or in, a transcription.

Referring to FIG. 6 and with further reference to FIGS. 1-3, process 130 of searching for data associated with desired data types using the system 10 includes the stages shown. The process 130, however, is exemplary only in not limiting. The process 130 can be altered, e.g, by having stages added, removed or rearranged.

At stage 132, a request for a data search is received. A user can enter a data search request through the administration console 18. For example, a healthcare provider might use a software application that queries the database 40 for all of the patient's peak pulse values for cardiac stress tests taken over a period of time. Alternatively, healthcare researchers may ask for the blood pressure values of numerous patients so that the researcher might judge the efficacy of a certain treatment regimen. The data request is forwarded through the network 22 to the database server 24 to be performed on the information stored on the database 40.

At stage 134, an inquiry is made as to whether data of the data types to be searched for are stored in separate data fields separate from transcriptions stored in the database 40. In particular, the database server 24 can determine whether database fields corresponding to the data types to be searched are stored in the database 40. If not, then the process 130 proceeds to stage 138 described below and otherwise proceeds to stage 136.

At stage 136, the database server 24 searches the stored database fields for data corresponding to the search request. The server 24 searches through stored data, e.g., the database 82 for data corresponding to data types indicated by the search request. For example, the server 24 may search for data corresponding to age, gender, and blood pressure corresponding to specific worktype codes entered or otherwise provided by the speaker when producing the dictation leading to a transcription.

At stage 138, the database server 24 searches stored transcriptions for the desired data corresponding to the indicated data type to be searched. The database server 24 may search the stored transcriptions as edited by a medical transcriptionist using the editing device 20. In this case, the server may employ the NLP module 42 to search through the stored transcriptions using appropriate trigger phrases and/or trigger models. The transcriptions are normalized by having portions formatted in structured tables, although the tables may differ. In this case, the trigger phrases and/or trigger models may be adapted to a search for text associated with structured tables of data, with the text associated with the structured tables potentially being different than trigger phrases that may be used in transcription. For example, in dictations, the speaker may say something like, "The patient is a 47-year-old male." The trigger phrase searched for in raw text may be a phrase such as "the patient is a," because this is a typical spoken lead-in to an age description, while a trigger phrase for searching in a normalized transcription may be more succinct, such as "age" or "gender" or "sex" as these are more likely to appear in a table.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. For example, the NLP module 42 may be disposed wholly or partially elsewhere (i.e., other than at the automatic transcription device 30), such as at the database server 24.

In other embodiments, for example, the NLP processing may take place after the MT has edited the original raw text transcription produced by the ASR device 30. Thus, referring to FIG. 5, the editing stage 118 may be performed before the NLP processing stage 116. In this instance, the MT may make no attempt to fill in the table format. This table may not be available to the MT at all. Instead, the MT corrects the raw speech recognition as usual and instructs the edited transcription to be stored. The stored edited transcription is analyzed by the NLP module 42 to perform the NLP processing stage 116. The trigger phrase and content models may be much more restrictive than in cases where the raw text is used as an input since the edited text is presumably more error free than the raw text transcription.

In other embodiments, a combination of techniques discussed above can be used. For example, a process may proceed according to stages 112, 114 and 116 shown in FIG. 5. In the editing stage, however, the medical transcriptionist may correct speech recognition and formatting errors but not move data into table fields or edit the tables fields and may not delete any of the transcribed text. The NLP module 42 may be applied to analyze the edited transcription with the further constraint that already filled-in table fields should not be located. Thus, the NLP module 42 would search over the remaining, non-table raw text for a subset of the original table fields that were neither filled in by the original analysis by the NLP module 42 nor filled in during the editing performed by the medical transcriptionist.

While the description above focused on medical transcriptions, the invention is not limited to medical transcriptions. The invention may be applied to data extraction for non-medical applications such as legal dictations (e.g., for billing), student evaluations (e.g., situations involving ratings and/or test scores including psychological evaluations), etc.

Further, while the discussion above refers to "the invention," more than one invention may be disclosed.

What is claimed is:

1. A computer-readable storage medium storing computer-executable instructions that, when executed by at least one processor of a computer, perform a method of providing a formatted transcription from an original transcription related to patient data, the method comprising:
   accessing a table comprising a plurality of fields associated with content of the original transcription, each of the plurality of fields corresponding to a data type and associated with at least one trigger phrase;
   processing the original transcription to determine whether there are any trigger phrases associated with one of the plurality of fields located in the original transcription; and
   for each trigger phrase located in the original transcription:
      determining whether text disposed proximately to the located trigger phrase in the original transcription includes data of the data type corresponding to the field associated with the located trigger phrase; and
      including the field associated with the located trigger phrase in the formatted transcription in association with the data identified as being of the data type corresponding to the field.

2. The computer-readable storage medium of claim 1, further comprising instructions for causing the computer to alter a format of the transcription based upon whether the data indicated by the text disposed proximately to the trigger phrase is of the desired type.

3. The computer-readable storage medium of claim 2, further comprising instructions for causing the computer to:
   obtain a set of indicia of desired data types to be determined; and
   store data type indicators, and corresponding indicia of data from the transcription determined to be of desired types, in the transcription indicative of a table format such that if the transcription is displayed, the data indicia are displayed in association with corresponding data type indicators.

4. The computer-readable storage medium of claim 3, wherein the instructions allow for the determination of data corresponding to less than all of the desired data types indicated by the set of indicia, whereby the computer program product provides for sparse data extraction.

5. The computer-readable storage medium of claim 2, wherein the instructions for causing the computer to obtain the set of indicia cause the computer to retrieve the set in accordance with a worktype associated with the transcription.

6. The computer-readable storage medium of claim 1, wherein the data indicated by the text disposed proximately to the trigger phrase is determined to be of the desired type only if a probability of the proximately-disposed data being of the desired type exceeds a threshold probability.

7. The computer-readable storage medium of claim 1, wherein the data indicated by the text disposed proximately to the trigger phrase is determined to be of a first data type if a first probability that the proximately-disposed data is of the first data type exceeds a second probability that the proximately-disposed data is of a second data type.

8. The computer-readable storage medium of claim 1, further comprising instructions for causing the computer to analyze information associated with patient to determine which type of data the indicated data are based on known relationships between values of different data types and patient information.

9. The computer-readable storage medium of claim 8, further comprising instructions for causing the computer to obtain the information associated with the patient from the transcription.

10. The computer-readable storage medium of claim 1, further comprising instructions for causing the computer to analyze the indicated data to determine which type of data the indicated data are based on known values of data associated with different data types.

11. The computer-readable storage medium of claim 1, further comprising instructions for causing the computer to remove from the transcription, if it is determined that data indicated by text disposed proximately to the trigger phrase is of a desired type, the proximately-disposed text and the trigger phrase.

12. The computer-readable storage medium of claim 1, further comprising instructions for causing the computer to modify the trigger phrase associated with the data type desired to be determined from the transcription.

13. The computer-readable storage medium of claim 1, wherein the instructions for causing the computer to determine if data indicated by text disposed proximately to the trigger phrase is of the desired type is capable of determining substantive data content of the text despite different phrases potentially forming the text.

14. The computer-readable storage medium of claim 1, wherein the formatted transcription is an edited version of the original transcription.

15. The computer-readable storage medium of claim 1, wherein the formatted transcription is a separate document from the original transcription.

16. A computer-implemented method for providing a formatted transcription from an original transcription related to patient data, the computer-implemented method comprising using at least one processor to:
    access a table comprising a plurality of fields associated with content of the original transcription, each of the plurality of fields corresponding to a data type and associated with at least one trigger phrase;
    process the original transcription to determine whether there are any trigger phrases associated with one of the plurality of fields located in the original transcription; and
    for each trigger phrase located in the original transcription:
        determine whether text disposed proximately to the located trigger phrase in the original transcription includes data of the data type corresponding to the field associated with the located trigger phrase; and
        include the field associated with the located trigger phrase in the formatted transcription in association with the data identified as being of the data type corresponding to the field.

17. The computer-implemented method of claim 16, wherein determining whether the text disposed proximately to the located trigger phrase in the original transcription includes the data of the data type corresponding to the field includes making a probabilistic determination as to whether the data is of the data type corresponding to the field at least in part by comparing the data to at least one value associated with the data type.

18. The computer-implemented method of claim 17, further comprising selecting the at least one value dependent upon patient information associated with a patient corresponding to the original transcription.

19. The computer-implemented method of claim 16, further comprising producing a table including indicia of data types and the data associated with the indication of the data type.

20. The computer-implemented method of claim 16, further comprising storing the data in a database field independent of the formatted transcription.

21. The computer-implemented method of claim 16, wherein the trigger phrase comprises a natural language phrase.

22. The computer-implemented method of claim 16, wherein at least a portion of the formatted transcription is normalized and the trigger phrase comprises a normalized language phrase.

23. The computer-implemented method of claim 16, wherein including the field further comprises removing the located trigger phrase from the original transcription.

24. The computer-implemented method of claim 16, wherein determining whether the text disposed proximately to the located trigger phrase in the original transcription includes the data of the data type corresponding to the field includes determining that a first probability that the data represents the data type exceeds a second probability that the data represents another data type.

25. The computer-implemented method of claim 16, wherein determining whether the text disposed proximately to the located trigger phrase in the original transcription includes the data of the data type corresponding to the field includes determining that a probability that the data represents the data type exceeds a probability threshold.

26. The computer-implemented method of claim 16, further comprising:
    when it is determined that text disposed proximately the located trigger phrase includes the data of the data type corresponding to the field associated with the located trigger phrase, modifying the original transcription to provide the formatted transcription at least in part by:
    replacing the located trigger phrase with the field.

27. The computer-implemented method of claim 16, wherein the formatted transcription is an edited version of the original transcription.

28. The method of claim 16, wherein the formatted transcription is a separate document from the original transcription.

29. A system comprising:
    at least one storage medium storing an original transcription related to patient data and a table comprising a plurality of fields associated with content of the original transcription, each of the plurality of fields corresponding to a data type and associated with at least one trigger phrase; and
    at least one processor capable of accessing the at least one storage medium, the at least one processor configured to:
        access the table;
        process the original transcription to determine whether there are any trigger phrases associated with one of the plurality of fields located in the original transcription; and for each trigger phrase located in the original transcription:
- determine whether text disposed proximately to the located trigger phrase in the original transcription includes data of the data type corresponding to the field associated with the located trigger phrase; and
- include the field associated with the located trigger phrase in a formatted transcription in association with the data identified as being of the data type corresponding to the field.

\* \* \* \* \*